(12) United States Patent
Momma et al.

(10) Patent No.: US 12,733,851 B2
(45) Date of Patent: Sep. 15, 2026

(54) DIAGNOSIS IMAGE READING CONTROL APPARATUS, DIAGNOSIS IMAGE READING CONTROL METHOD, AND NON-TRANSITORY COMPUTER-READABLE STORAGE MEDIUM

(71) Applicant: JVCKENWOOD Corporation, Yokohama (JP)

(72) Inventors: Yuki Momma, Yokohama (JP); Hiroyuki Takei, Yokohama (JP); Yoshiya Miyasaka, Yokohama (JP); Kaoru Fujita, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 240 days.

(21) Appl. No.: 18/403,783

(22) Filed: Jan. 4, 2024

(65) Prior Publication Data

US 2024/0138735 A1 May 2, 2024

Related U.S. Application Data

(63) Continuation of application No. PCT/JP2022/028666, filed on Jul. 25, 2022.

(30) Foreign Application Priority Data

Jul. 29, 2021 (JP) ................................ 2021-124618

(51) Int. Cl.
*A61B 5/00* (2006.01)
*A61B 5/16* (2006.01)

(52) U.S. Cl.
CPC ........... *A61B 5/163* (2017.08); *A61B 5/7425* (2013.01)

(58) Field of Classification Search
None
See application file for complete search history.

(56) References Cited

U.S. PATENT DOCUMENTS

| | | | | |
|---|---|---|---|---|
| 9,390,682 | B2 * | 7/2016 | Hadas | G09G 3/30 |
| 9,913,349 | B2 * | 3/2018 | Kano | H05B 47/115 |
| 9,990,035 | B2 * | 6/2018 | Richmond | G06F 3/04845 |
| 10,558,263 | B2 * | 2/2020 | Aoyama | G16H 30/20 |

(Continued)

FOREIGN PATENT DOCUMENTS

JP 2013-254358 12/2013

OTHER PUBLICATIONS

International Search Report and Written Opinion for International Application No. PCT/JP2022/028666 mailed on Sep. 13, 2022, 8 pages.

*Primary Examiner* — Shirley X Jian
(74) *Attorney, Agent, or Firm* — Amin, Turocy & Watson, LLP

(57) ABSTRACT

A diagnosis image reading control apparatus includes: a display controller configured to perform control to display multiple images on a display; a detector configured to detect a line of sight of a user on the display; a region determination unit configured to determine where the line of sight of the user is positioned in multiple regions divided in each of the images; and a luminance adjustment unit configured to adjust luminance of the images, wherein the luminance adjustment unit is further configured to adjust to increase luminance of the region designated by the line of sight of the user in the images.

5 Claims, 8 Drawing Sheets

(56) References Cited

U.S. PATENT DOCUMENTS

| | | | | |
|---|---|---|---|---|
| 12,033,558 | B2 * | 7/2024 | Ko | G09G 5/10 |
| 2005/0180740 | A1 * | 8/2005 | Yokoyama | G09G 5/00<br>396/421 |
| 2011/0270123 | A1 * | 11/2011 | Reiner | A61B 6/469<br>600/558 |
| 2011/0273466 | A1 * | 11/2011 | Imai | G09G 3/20<br>345/589 |
| 2013/0135494 | A1 * | 5/2013 | Kim | H04N 23/673<br>348/333.01 |
| 2015/0055808 | A1 * | 2/2015 | Vennstrom | G06F 3/012<br>381/307 |
| 2015/0058812 | A1 * | 2/2015 | Lindh | H04S 7/308<br>715/863 |
| 2015/0116203 | A1 * | 4/2015 | Narita | G06T 5/70<br>345/156 |
| 2015/0269907 | A1 * | 9/2015 | Hadas | G09G 5/363<br>345/589 |
| 2016/0246384 | A1 * | 8/2016 | Mullins | G06F 3/017 |
| 2016/0334868 | A1 * | 11/2016 | Pacheco | G06F 3/013 |
| 2017/0132488 | A1 * | 5/2017 | Asanuma | G09G 3/2092 |
| 2018/0136719 | A1 * | 5/2018 | Chen | G06F 3/013 |
| 2020/0074941 | A1 * | 3/2020 | Takahashi | G09G 3/36 |
| 2021/0082371 | A1 * | 3/2021 | Novelli | G09G 5/10 |
| 2022/0394234 | A1 * | 12/2022 | Etigson | G02B 30/10 |
| 2024/0138735 | A1 * | 5/2024 | Momma | G09G 5/00 |
| 2025/0117076 | A1 * | 4/2025 | Strandborg | G06V 40/193 |

* cited by examiner

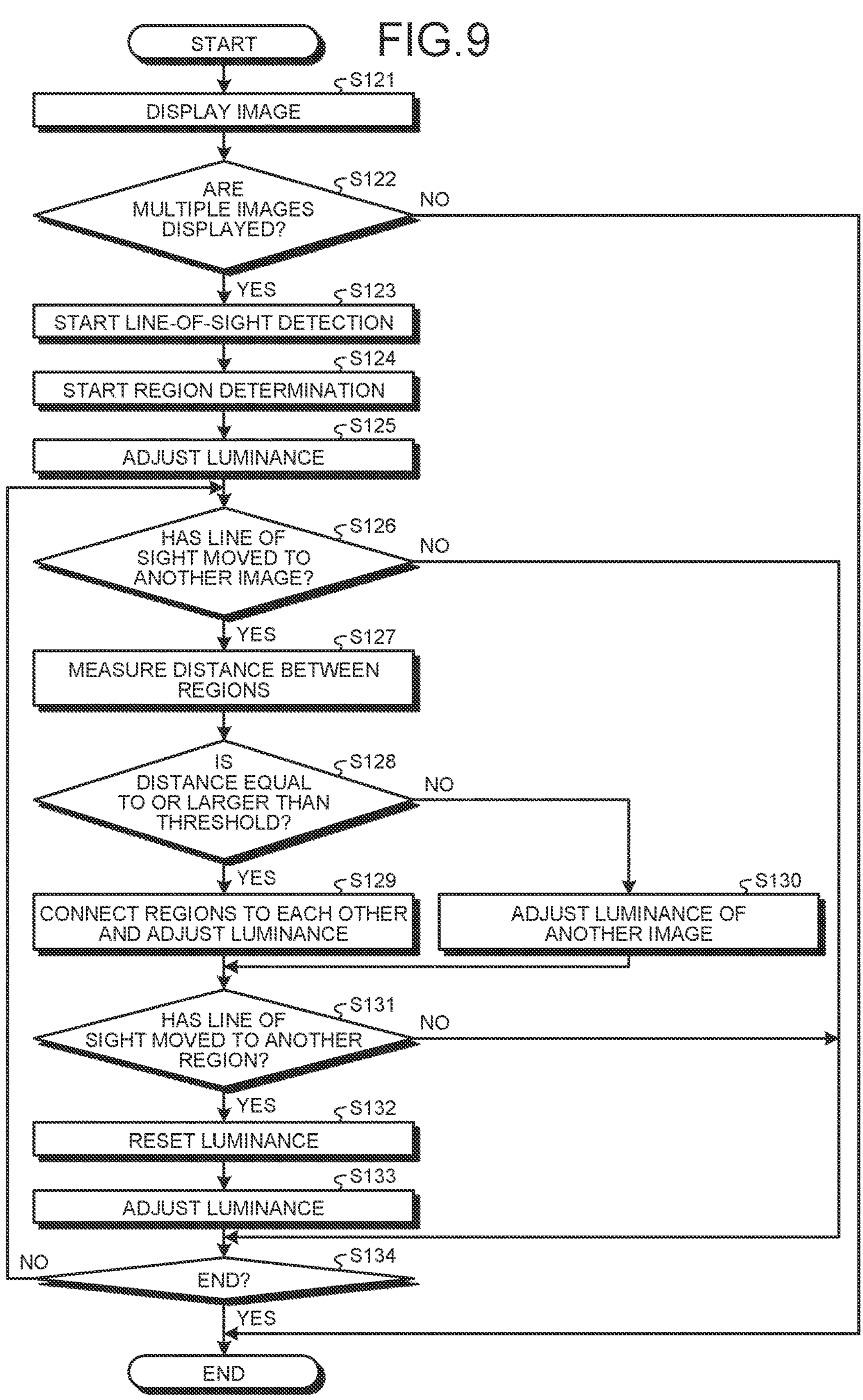
FIG.9
START
S121
DISPLAY IMAGE
S122
ARE MULTIPLE IMAGES DISPLAYED?
NO
YES
S123
START LINE-OF-SIGHT DETECTION
S124
START REGION DETERMINATION
S125
ADJUST LUMINANCE
S126
HAS LINE OF SIGHT MOVED TO ANOTHER IMAGE?
NO
YES
S127
MEASURE DISTANCE BETWEEN REGIONS
S128
IS DISTANCE EQUAL TO OR LARGER THAN THRESHOLD?
NO
YES
S129
CONNECT REGIONS TO EACH OTHER AND ADJUST LUMINANCE
S130
ADJUST LUMINANCE OF ANOTHER IMAGE
S131
HAS LINE OF SIGHT MOVED TO ANOTHER REGION?
NO
YES
S132
RESET LUMINANCE
S133
ADJUST LUMINANCE
S134
NO
END?
YES
END

FIG.11

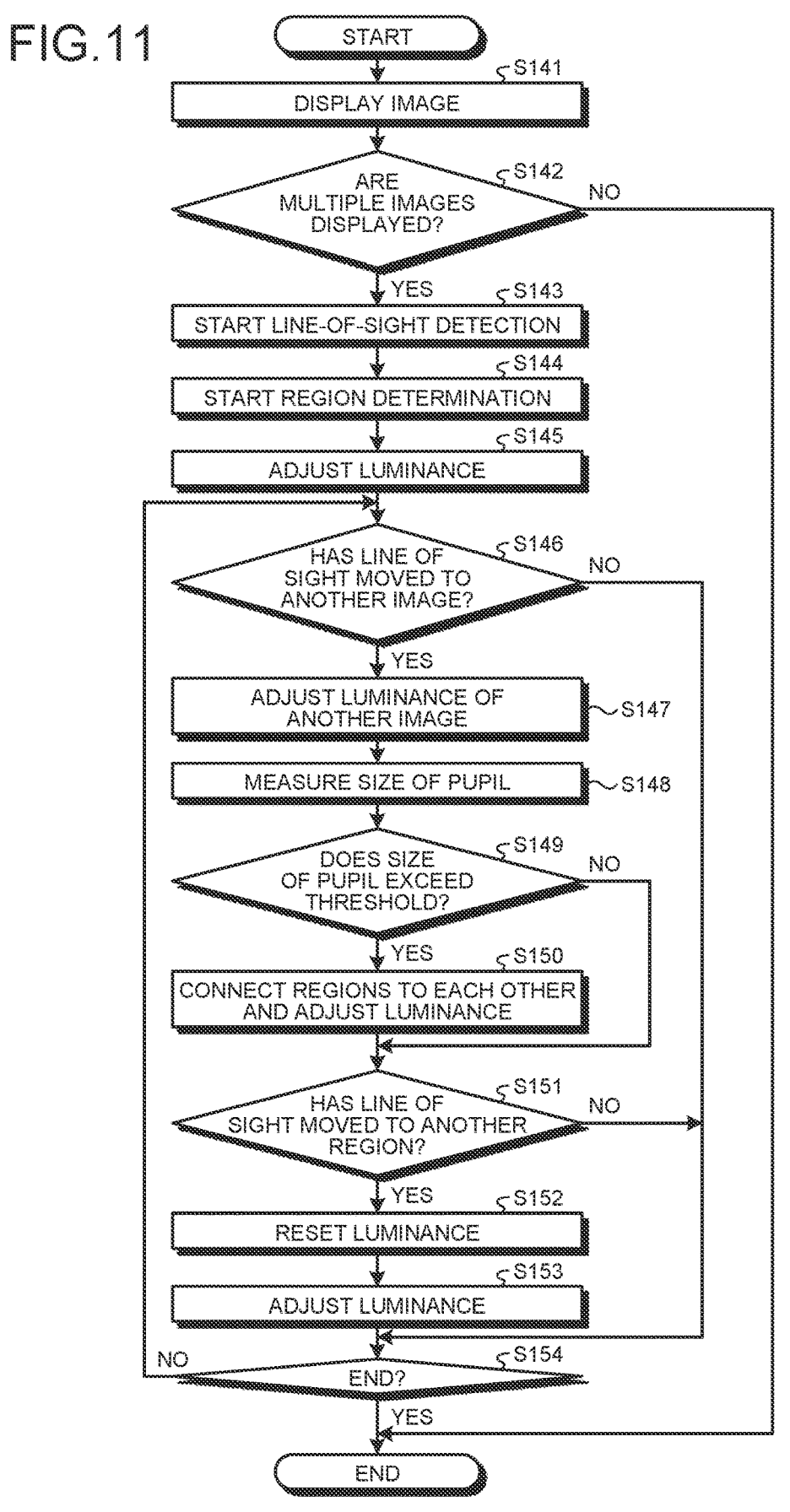

START
S141 DISPLAY IMAGE
S142 ARE MULTIPLE IMAGES DISPLAYED?
NO
YES
S143 START LINE-OF-SIGHT DETECTION
S144 START REGION DETERMINATION
S145 ADJUST LUMINANCE
S146 HAS LINE OF SIGHT MOVED TO ANOTHER IMAGE?
NO
YES
S147 ADJUST LUMINANCE OF ANOTHER IMAGE
S148 MEASURE SIZE OF PUPIL
S149 DOES SIZE OF PUPIL EXCEED THRESHOLD?
NO
YES
S150 CONNECT REGIONS TO EACH OTHER AND ADJUST LUMINANCE
S151 HAS LINE OF SIGHT MOVED TO ANOTHER REGION?
NO
YES
S152 RESET LUMINANCE
S153 ADJUST LUMINANCE
S154 END?
NO
YES
END

DIAGNOSIS IMAGE READING CONTROL APPARATUS, DIAGNOSIS IMAGE READING CONTROL METHOD, AND NON-TRANSITORY COMPUTER-READABLE STORAGE MEDIUM

CROSS-REFERENCE TO RELATED APPLICATIONS

This application is a Continuation of PCT International Application No. PCT/JP2022/028666 filed on Jul. 25, 2022 which claims the benefit of priority from Japanese Patent Application No. 2021-124618 filed on Jul. 29, 2021, the entire contents of both of which are incorporated herein by reference.

BACKGROUND OF THE INVENTION

The present application relates to a diagnosis image reading control apparatus, a diagnosis image reading control method, and a non-transitory storage medium.

There is known a technology for adjusting, in accordance with a gazing point of a user, luminance of an image content including multiple image contents with different luminance (refer to Japanese Patent Application Laid-open No. 2013-254358, for example).

In a diagnosis image reading apparatus for displaying images to be read, diagnosis image reading is performed in a darkened room, and thus when luminance of a screen is high, a risk of causing eyestrain increases. With the technology of Japanese Patent Application Laid-open No. 2013-254358, the luminance of an entire screen increases, which is not desirable as the diagnosis image reading apparatus. Also known is a method of adjusting the luminance of the diagnosis image reading apparatus by an operation on an input device such as a mouse, but it is desirable to adjust the luminance in a more intuitive manner.

A diagnosis image reading control apparatus, a diagnosis image reading control method, and a non-transitory storage medium are disclosed.

SUMMARY OF THE INVENTION

According to one aspect of the present application, there is provided a diagnosis image reading control apparatus comprising: a display controller configured to perform control to display multiple images on a display; a detector configured to detect a line of sight of a user on the display; a region determination unit configured to determine where the line of sight of the user is positioned in multiple regions divided in each of the images; and a luminance adjustment unit configured to adjust luminance of the images, wherein the luminance adjustment unit is further configured to adjust to increase luminance of the region designated by the line of sight of the user in the images.

According to one aspect of the present application, there is provided a diagnosis image reading control method comprising: performing control to display multiple images on a display; detecting a line of sight of a user on the display; determining where the line of sight of the user is positioned in multiple regions divided in each of the images; and adjusting luminance of the images, wherein the adjusting further comprising adjusting to increase luminance of the regions designated by the line of sight of the user in the images.

According to one aspect of the present application, there is provided a non-transitory storage medium that stores a computer program executed by a computer operating as a diagnosis image reading apparatus, the computer program comprising: performing control to display multiple images on a display; detecting a line of sight of a user on the display; determining where the line of sight of the user is positioned in multiple regions divided in each of the images; and adjusting luminance of the images, wherein the adjusting further comprising adjusting to increase luminance of the regions designated by the line of sight of the user in the images.

The above and other objects, features, advantages and technical and industrial significance of this application will be better understood by reading the following detailed description of presently preferred embodiments of the application, when considered in connection with the accompanying drawings.

BRIEF DESCRIPTION OF THE DRAWINGS

FIG. 9 is a flowchart of an example of processes in the diagnosis image reading control apparatus according to the second embodiment;

FIG. 11 is a flowchart of an example of processes in the diagnosis image reading control apparatus according to the third embodiment.

DETAILED DESCRIPTION OF THE INVENTION

The following describes embodiments of a diagnosis image reading control apparatus, a diagnosis image reading control method, and a non-transitory storage medium according to the present application based on the accompanying drawings. The following embodiments do not limit the present application.

First Embodiment

Diagnosis Image Reading Apparatus

Figure 1:
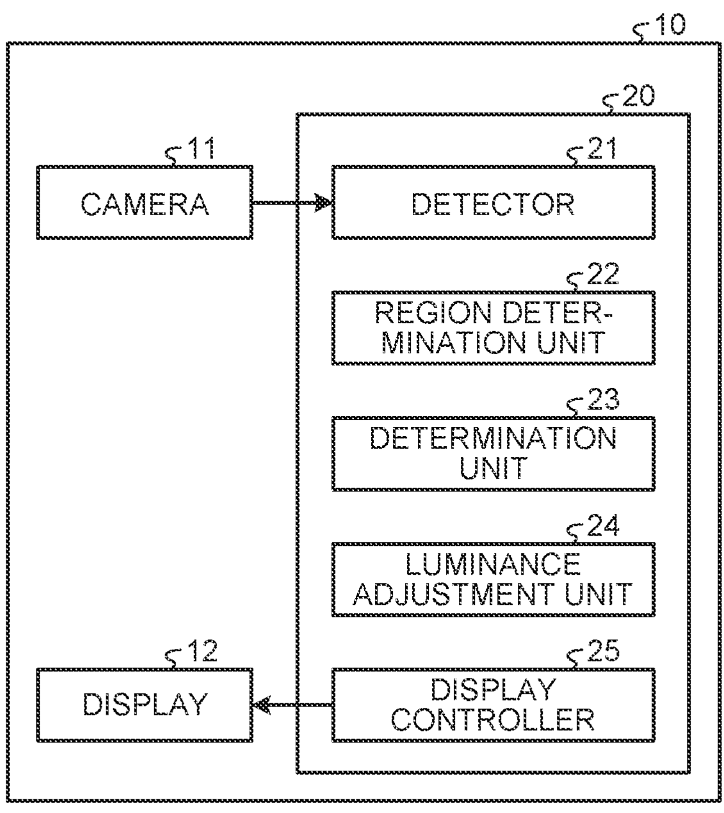
FIG. 1 is a block diagram of a configuration example of a diagnosis image reading apparatus having a diagnosis image reading control apparatus according to a first embodiment.

FIG. 1 is a block diagram of a configuration example of a diagnosis image reading apparatus 10 having a controller 20 according to a first embodiment. The diagnosis image reading apparatus 10 is an apparatus used for reading images to be read in radiography or mammography, for example. During diagnosis image reading, the diagnosis image reading apparatus 10 detects line-of-sight position information indicating a line-of-sight position of a user on a display 12. The diagnosis image reading apparatus 10 partially adjusts, in accordance with the line-of-sight position information, the luminance of the images to be read to display the images to be read in accordance with the line-of-sight position information. The diagnosis image reading apparatus 10 has a camera 11, the display 12, and a controller (a diagnosis image reading control apparatus) 20.

In the present embodiment, multiple images are multiple images to be read which are placed side by side for diagnosis image reading and visually compared with each other. The images are, for example, images to be read of the same part of a human body. The images may be stored as multiple image data files. The images may be stored as a single image data file. The present embodiment describes a case in which there are two images.

The camera 11 is a camera capture an image of a user. The camera 11 is disposed at a position from which an image of a face of the user who visually recognizes the display 12 of the diagnosis image reading apparatus 10 can be captured. The camera 11 includes, for example, a visible light camera, a far-infrared camera, or a near-infrared camera. The camera 11 may include, for example, a combination of the visible light camera and the far-infrared or the near-infrared camera. The camera 11 constantly captures a user image while the images are displayed. The camera 11 outputs the captured user image to a detector 21 of the controller 20.

The display 12 is an apparatus for displaying various types of information. The display 12 is a display including, for example, a liquid crystal display (LCD) or an organic electro-luminescence (EL) display. The display 12 displays images based on an image signal output from a display controller 25 of the controller 20. In the present embodiment, the display 12 displays images to be read. The display 12 displays the images to be read with the luminance adjusted in accordance with the line-of-sight position of the user.

The display 12 displays multiple images. The display 12 has a vertical or horizontal display screen. One or multiple displays 12 are provided. The displays 12 may be arranged with no gaps between them or arranged spaced about a few centimeters apart. The displays 12 may be arranged side by side, and the display s 12 may show different images. One display 12 may display multiple images side by side.

Displaying multiple images separately means displaying the images side by side so that they can be comparted with each other. The images may be displayed partially overlapping with each other so long as they can be compared with each other.

The controller 20 is an arithmetic processing unit (control apparatus) including, for example, a central processing unit (CPU). The controller 20 loads a stored computer program into a memory and executes commands included in the computer program. The controller 20 includes an internal memory not illustrated. The internal memory is used for temporary storage of data in the controller 20 and the like. The controller 20 detects the line-of-sight position information indicating the line-of-sight position of the user on the display 12 during diagnosis image reading. The controller 20 performs control to adjust, in accordance with the line-of-sight position information, the luminance of the images to be read to display the images to be read. The controller 20 has the detector 21, a region determination unit 22, a determination unit 23, a luminance adjustment unit 24, and the display controller 25.

The detector 21 detects the line-of-sight position of the user on the display 12. The detector 21 detects the line-of-sight position of the user on the display 12 on which the images in the diagnosis image reading apparatus 10 used by the user are displayed. In the present embodiment, the detector 21 detects the line-of-sight position of the user on an image, which indicates where the user looks at in the image. The detector 21 acquires a user image from the camera 11. The detector 21 performs an image processing on the acquired user image to detect the line-of-sight of the user on the display 12 base on an image of the eye of the user. The detector 21 detects the line of sight of the user by various methods such as a detection of the line of sight based on a position of a pupil and a position of a corneal reflection image of the user and a detection of the line of sight based on a position of an eye socket and a position of an iris of the user. In this way, the detector 21 detects the line-of-sight position information indicating the position of the line of sight of the user on the image.

The region determination unit 22 determines where the line of sight of the user is positioned in regions divided in each of the images. The region determination unit 22 determines a line-of-sight region, which is a region in which the line of sight of the user is positioned on the image, based on the line-of-sight position information detected by the detector 21. The line-of-sight region is a region designated by the line of sight of the user. The following describes determination of the line-of-sight region.

The region determination unit 22 may, for example, divide a display screen of the display 12 into multiple regions, determine a region in which the line-of-sight position of the user exists, and output the determined region as the line-of-sight region. In the present embodiment, the region determination unit 22 divides the display screen of the display 12 into the regions. The region determination unit 22 may, for example, divide the image displayed on the display screen of the display 12 into multiple regions, determine a region in which the line-of-sight position of the user exists, and output the determined region as the line-of-sight region. The region determination unit 22 determines in which region the line-of-sight position detected by the detector 21 is positioned. An area of the region may be varied in accordance with a size of the display screen of display 12 or a size of an area of the image being displayed. For example, a larger area of the display screen or the image may have a larger area of the region.

The region determination unit 22 may, for example, determine a region with a certain shape such as a rectangular shape or a circular shape centered on the line-of-sight position of the user and output the determined region as the line-of-sight region, in which the line-of-sight position of the user exists. The area of the region with a certain shape may be varied in accordance with the size of the display screen of the display 12 or the size of the area of the image being displayed. For example, a larger area of the display screen or the image may have a larger area of the region with a certain shape.

The region determination unit 22 may, for example, determine a region identified by the user by movement of the line-of-sight position on the image and output the determined region as the line-of-sight region, in which the line-of-sight position of the user exists. The region determination unit 22 may, for example, determine a rectangular region with a straight line along which the user has moved the line-of-sight position as a diagonal line on the image and output the determined region as the line-of-sight region, in which the line-of-sight position of the user exists.

The region determination unit 22 may output a region in which the line-of-sight position of the user is determined to have remained for a certain threshold time or longer as the line-of-sight region.

The determination unit 23 determines a number of images displayed on the display 12. The determination unit 23 may, for example, determine that multiple images are displayed when multiple images are displayed on a single display 12. The determination unit 23 may, for example, determine that multiple images are displayed when multiple images are displayed on multiple displays 12 respectively.

The determination unit 23 may determine that the multiple images are displayed on the display 12 based on an image signal output from the display controller 25, for example. The determination unit 23 may determine that multiple images are displayed on the display 12 based on a frame or the like which indicates a boundary between the images and which is detected by performing an image recognition process on the images displayed on the display 12, for example. The determination unit 23 may determine that multiple images are displayed on the display 12 based on imaged objects included in the images and detected by performing an image recognition processing on the images displayed on the display 12, for example. The determination unit 23 may determine that multiple images are displayed on the display 12 based on a number of images selected to be displayed on the display 12, based on operational information from an operating unit not illustrated, for example. For a method for recognizing the number of images being displayed on the display 12 by the determination unit 23, a known method can be used without limitation.

The luminance adjustment unit 24 adjusts luminance of an image. Upon designation of a region in the image by the line of sight of the user, the luminance adjustment unit 24 adjusts brightness so as to reduce the overall luminance of the screen from an initial state. More specifically, when it is determined that the multiple images are displayed by the determination unit 23, the luminance adjustment unit 24 adjust to increase the luminance of respective regions designated by the line of sight of the user for the images. For an image to which the user is paying attention, the luminance adjustment unit 24 adjusts to increase the luminance of a region designated by the line of sight of the user than the luminance outside the region. The luminance adjustment unit 24 reduces the luminance outside the region than the luminance in the initial state in which the multiple images are displayed on the display 12 to adjust brightness. Then, when the line of sight of the user moves to another image, the adjustment of the luminance for the original image before the movement of the line of sight remains maintained. Then, in the another image to which the line of sight of the user has moved, the luminance adjustment unit 24 adjusts to increase the luminance of the region designated by the line of sight of the user than the luminance outside the region. In this way, the luminance of the respective regions of the images is increased.

The luminance adjustment unit 24 generates a control signal for controlling the luminance of a backlight of the display 12. The luminance adjustment unit 24 outputs a control signal for making the luminance of the region higher than the luminance outside the region. Increasing the luminance of the backlight increases the luminance of the screen when the images are displayed on the display 12. Lowering the luminance of the backlight lowers the luminance of the screen when the images are displayed on the display 12.

Alternatively, the luminance adjustment unit 24 generates an image in which brightness of each pixel of the image is adjusted. The luminance adjustment unit 24 generates an image in which brightness of pixels in the region of the image is higher than brightness of pixels outside the region. In this case, the image the brightness of which has been corrected by the luminance adjustment unit 24 is displayed on the display 12 by the display controller 25.

The luminance adjustment unit 24 resets the luminance of the image. More specifically, the luminance adjustment unit 24 resets the luminance when it determines that the line of sight of the user has moved. For example, when, with the luminance of a region of one image being adjusted, the line of sight of the user moves to another region in the image, the region for which the luminance is adjusted of the image changes in accordance with the line of sight. For example, when, with the luminance of regions of the images being adjusted, the line of sight of the user moves to another region, the luminance of the regions of the images is reset. Then, in the image in which the line of sight has moved to the another region, the luminance of the region designated by line of sight of the user is adjusted to be increased. Resetting the luminance of the image is restoring a state of the initial luminance of the image.

The display controller 25 performs control to display multiple images on the display 12. The display controller 25 performs control to display the images separately on the display 12. The display controller 25, for example, performs control to display the images separately for one display 12. In other words, the display controller 25, for example, performs control to display the images side by side for one display 12. The display controller 25, for example, performs control to display different images for multiple displays 12 respectively. The display controller 25 performs control to display an image the luminance of which has been adjusted by the luminance adjustment unit 24. The display controller 25 outputs an image signal for outputting the image to the display 12.

Figure 2:
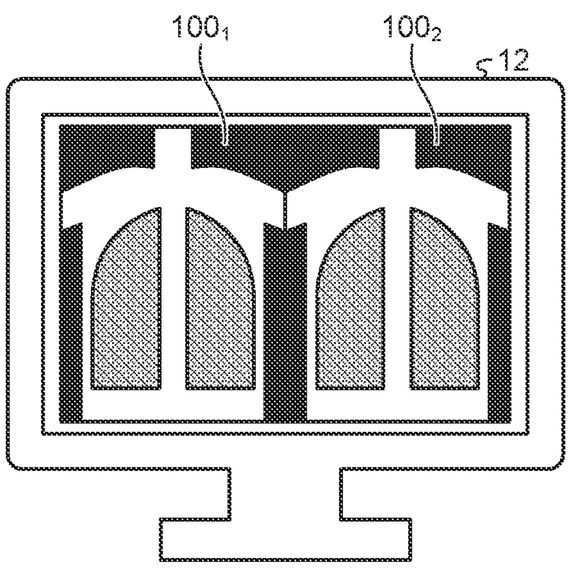
FIG. 2 is a diagram illustrating an example of an image displayed on a display.

FIG. 2 is a diagram illustrating an example of images 100 displayed on the display 12. In the present embodiment, one display 12 displays two images 100. In the state illustrated in FIG. 2, no region is designated by the line of sight of the user, and the luminance of the screen is in the initial state. The display 12 displays an image $\mathbf{100}_1$ and an image $\mathbf{100}_2$. In the image $\mathbf{100}_1$ and the image $\mathbf{100}_2$, the entire luminance is adjusted to be increased.

Figure 3:
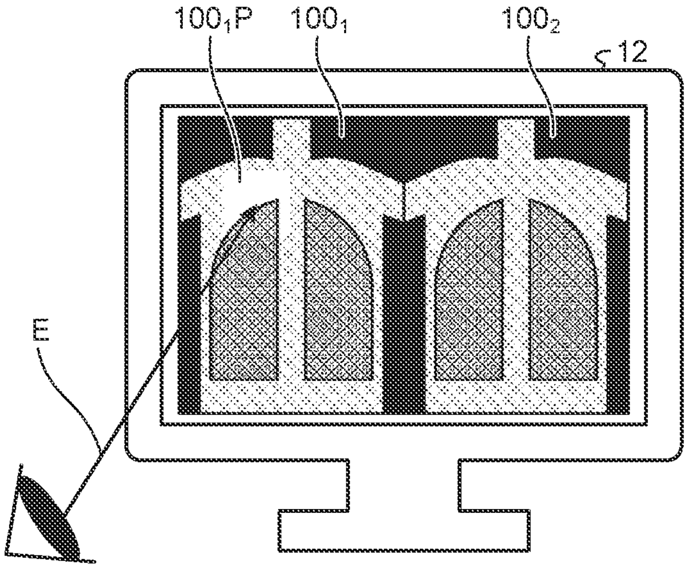
FIG. 3 is a diagram illustrating another example of the image displayed on the display.

FIG. 3 is a diagram illustrating another example of the images 100 displayed on the display 12. In the state illustrated in FIG. 3, a region is designated by a line of sight E of the user. In the image $\mathbf{100}_1$ and the image $\mathbf{100}_2$, the entire luminance is reduced to adjust brightness. In the image $\mathbf{100}_1$, the luminance is adjusted to be increased only in a region $\mathbf{100}_1$P at the upper left of the image $\mathbf{100}_1$ designated by the line of sight E of the user.

Figure 4:
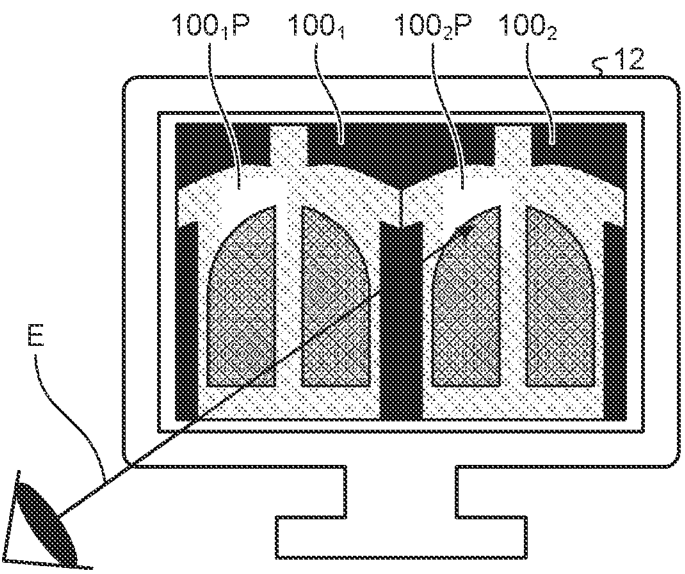
FIG. 4 is a diagram illustrating another example of the image displayed on the display.

FIG. 4 is a diagram illustrating another example of the images 100 displayed on the display 12. In the state illustrated in FIG. 4, a region is designated by a line of sight E of the user. In the image $\mathbf{100}_1$ and the image $\mathbf{100}_2$, the entire luminance is reduced to adjust brightness. In the image $\mathbf{100}_1$, the luminance is adjusted to be increased only in the region $\mathbf{100}_1$P designated by the line of sight E of the user in FIG. 3. In the image $\mathbf{100}_2$, the luminance is adjusted to be increased only in a region $\mathbf{100}_2$P designated by the line of sight E of the user. In this way, the luminance of the region $\mathbf{100}_1$P and the region $\mathbf{100}_2$P is increased.

Figure 5:
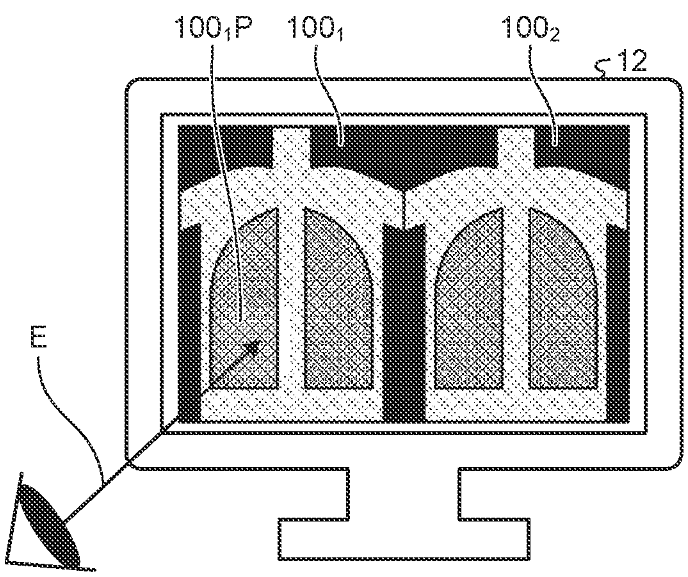
FIG. 5 is a diagram illustrating another example of the image displayed on the display.

FIG. 5 is a diagram illustrating another example of the images 100 displayed on the display 12. In the state illustrated in FIG. 5, a region is designated by a line of sight E of the user. In the image $\mathbf{100}_1$ and the image $\mathbf{100}_2$, the entire luminance is reduced to adjust brightness. In the image $\mathbf{100}_1$, the luminance is adjusted to be increased only in the region $\mathbf{100}_1$P at the lower left of the image $\mathbf{100}_1$ designated by the line of sight E of the user.

Processes in Diagnosis Image Reading Apparatus

Figure 6:
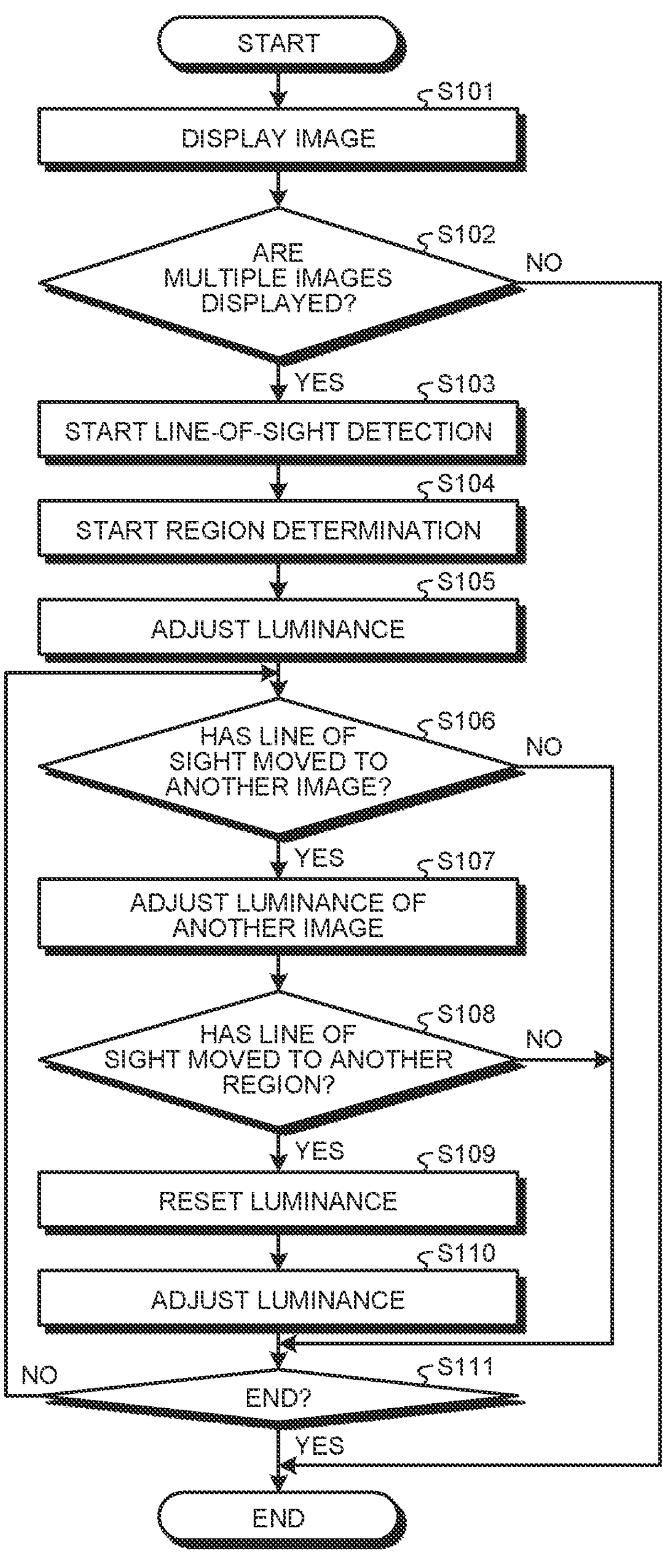
FIG. 6 is a flowchart of an example of processes in the diagnosis image reading control apparatus according to the first embodiment.

The following describes processes in the diagnosis image reading apparatus 10 by FIG. 6. FIG. 6 is a flowchart of an example of processes in the controller 20 according to the first embodiment. When the diagnosis image reading apparatus 10 is activated, and while a process for displaying the images on the display 12 is being performed, the processes of the flowchart illustrated in FIG. 6 is performed.

The controller 20 displays images (Step S101). More specifically, by the display controller 25, the controller 20 performs control to display the images separately on the display 12. In the present embodiment, the controller 20 causes the display controller 25 to display two images side by side on one display 12. The controller 20 proceeds to Step S102.

AT Step S101, the display 12 displays, for example, the image $\mathbf{100}_2$ and the image $\mathbf{100}_2$ illustrated in FIG. 2.

The controller 20 determines whether multiple images are displayed (Step S102). More specifically, by the determination unit 23, the controller 20 determines whether multiple images are displayed on the display 12, based on, for example, the image signal output from the display controller 25. By the determination unit 23, the controller 20 performs, for example, an image recognition process on the images displayed on the display 12 to detect a frame or the like indicating the boundary between the images and determine that multiple images are displayed. By the determination unit 23, the controller 20 performs, for example, an image recognition process on the images displayed on the display 12 to determine that multiple images are displayed, from imaged objects included in the images. By the determination unit 23, the controller 20 determines that multiple images are displayed based on the number of the images selected to be displayed on the display 12, based on, for example, the operational information from the operating unit not illustrated. If the determination unit 23 determines that multiple images are displayed (Yes at Step S102), the controller 20 proceeds to Step S103. If the determination unit 23 does not determine that multiple images are displayed (No at Step S102), the controller 20 ends the process.

If it is determined that multiple image are displayed (Yes at Step S102), the controller 20 starts line-of-sight detection (Step S103). More specifically, by the detector 21, the controller 20 performs an image processing on the user image to calculate the line-of-sight position of the user on the display 12 of the diagnosis image reading apparatus 10 used by the user. By the detector 21, the controller 20 calculates the line-of-sight position information indicating the line-of-sight position of the user on the image. The controller 20 proceeds to Step S104.

The controller 20 starts region determination (Step S104). More specifically, by the region determination unit 22, the controller 20 determines the region in which the line of sight of the user is positioned, based on the line-of-sight position information detected by the detector 21. The controller 20 proceeds to Step S105.

The controller 20 adjusts the luminance of the image (Step S105). More specifically, by the luminance adjustment unit 24, the controller 20 adjusts to increase the luminance of the region designated by the line of sight of the user for the image. The controller 20 proceeds to Step S106.

By Step S105, the display 12 displays, for example, the image $\mathbf{100}_1$ and the image $\mathbf{100}_2$ illustrated in FIG. 3. The luminance of the screen when the image $\mathbf{100}_1$ and the image $\mathbf{100}_2$ are displayed is reduced in overall luminance than in FIG. 2. The luminance is adjusted to be increased only in the region $\mathbf{100}_1$P at the upper left of the image $\mathbf{100}_1$.

The controller 20 determines whether the line of sight has moved to another image (Step S106). More specifically, by the detector 21, the controller 20 determines whether the line of sight of the user has moved to the another image, based on the line-of-sight position information detected. If it is determined that the line of sight has moved to the another image (Yes at Step S106), the controller 20 proceeds to Step S107. If it is not determined that the line of sight has moved to the another image (No at Step S106), the controller 20 proceeds to Step S111.

If it is determined that the line of sight has moved to the another image (Yes at Step S106), the controller 20 adjusts the luminance of the another image (Step S107). More specifically, by the luminance adjustment unit 24, the controller 20 adjusts to increase the luminance of the region designated by the line of sight of the user in the another image. The controller 20 proceeds to Step S108.

By Step S107, the display 12 displays, for example, the image $\mathbf{100}_2$ and the image $\mathbf{100}_2$ illustrated in FIG. 4. In addition to the region $\mathbf{100}_2$ P at the upper left of the image $\mathbf{100}_2$, in the region $\mathbf{100}_2$ P at the upper left of the image $\mathbf{100}_2$, the luminance is adjusted to be increased.

The controller 20 determines whether the line of sight has moved to another region (Step S108). More specifically, the controller 20 determines whether the line of sight of the user has moved to another region, based on the line-of-sight position information detected by the detector 21. The another region is, for example, a region other than the original image or the region the luminance of which has been adjusted of the another image. If it is determined that the line of sight has moved to another region (Yes at Step S108), the controller 20 proceeds to Step S109. If it is not determined that the line of sight has moved to another region (No at Step S108), the controller 20 proceeds to Step S111.

If it is determined that the line of sight has moved to another region (Yes at Step S108), the controller 20 resets the luminance (Step S109). More specifically, by the luminance adjustment unit 24, the controller 20 resets the luminance of the region adjusted by increasing the luminance of the screen in the image displayed on the display 12. The controller 20 proceeds to Step S110.

The controller 20 adjusts the luminance of the image (Step S110). More specifically, by the luminance adjustment unit 24, the controller 20 adjusts to increase the luminance of the another region designated by the line of sight of the user. The controller 20 proceeds to Step S111.

By Step S110, the display 12 displays, for example, the image $\mathbf{100}_1$ and the image $\mathbf{100}_2$ illustrated in FIG. 5. The luminance adjusted at Step S105 and Step S107 has been reset. The luminance is adjusted to be increased only in the region $\mathbf{100}_1$P at the lower left of the image $\mathbf{100}_1$.

The controller 20 determines whether to end the processes (Step S111). More specifically, the controller 20 determines to end the processes, for example, when an operation to end the processes for displaying the images is performed, when an operation to change the images to be displayed is performed, when a power of the diagnosis image reading apparatus 10 is turned off, or the like. If it is determined to end the processes (Yes at Step S111), the controller 20 ends the processes. If it is not determined to end the processes (No at Step S111), the controller 20 executes the processes at Step S106 again.

Effects

As described above, the present embodiment can increase and adjust the luminance only in the regions designated by the line of sight of the user in the images when multiple images are displayed on the display 12. The present embodiment can reduce an area of the region for which the luminance is increased. The present embodiment can adjust the luminance of the screen appropriately in accordance with the region of the image. The present embodiment can reduce eyestrain caused due to high luminance.

The present embodiment can designate regions by the line of sight of the user without requiring any operation to an input device by the user. The present embodiment enables intuitive designation of regions.

Second Embodiment

Figure 7:
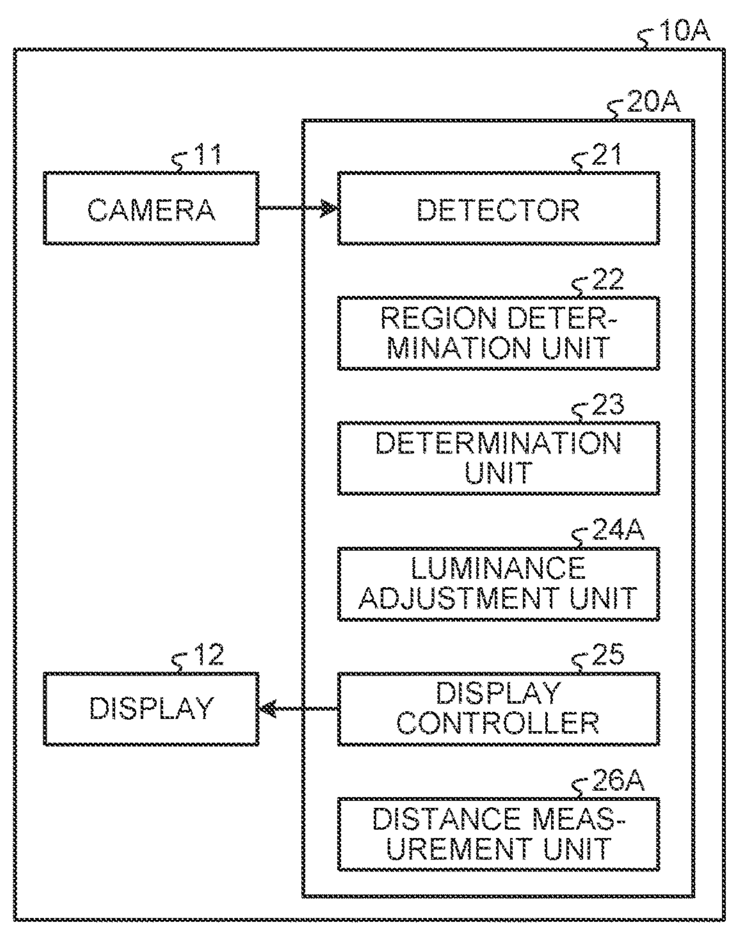
FIG. 7 is a block diagram of a configuration example of a diagnosis image reading apparatus having a diagnosis image reading control apparatus according to a second embodiment.
Figure 8:
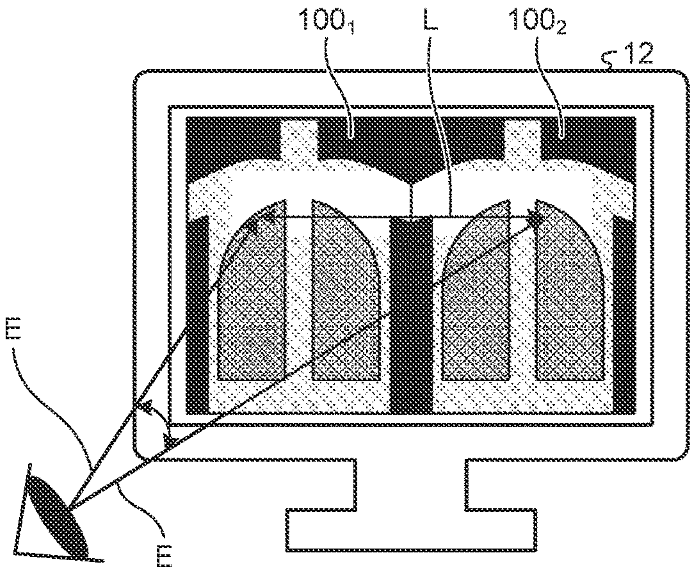
FIG. 8 is a diagram illustrating another example of the image displayed on the display.

The following describes a diagnosis image reading apparatus 10A having a controller 20A according to the present embodiment with reference to FIG. 7 to FIG. 9. FIG. 7 is a block diagram of a configuration example of the diagnosis image reading apparatus 10A having the controller 20A according to a second embodiment. FIG. 8 is a diagram illustrating another example of the images displayed on the display 12. FIG. 9 is a flowchart of an example of processes in the controller 20A according to the second embodiment. The diagnosis image reading apparatus 10A is similar to the diagnosis image reading apparatus 10 according to the first embodiment in its basic configuration. In the following description, components similar to those of the diagnosis image reading apparatus 10 are denoted by the same symbols or corresponding symbols, and detailed descriptions thereof are omitted. The controller 20A according to the present embodiment differs from that of the first embodiment in that the controller 20A has a distance measurement unit 26A and different processes in a luminance adjustment unit 24A.

The distance measurement unit 26A measures a distance between regions designated by the line of sight of the user for respective images. In the present embodiment, when the user designates regions in multiple images, the distance measurement unit 26A measures a distance between the respective regions. The method for measuring the distance between the regions may measure the distance between points at which a line connecting centers of the respective regions to each other intersects boundaries of the respective regions.

When the distance is equal to or larger than a threshold, the luminance adjustment unit 24A connects the respective regions of the images to each other and adjusts to increase the luminance. More specifically, when the distance is equal to or larger than the threshold based on the measurement result of the distance measurement unit 26A, the luminance adjustment unit 24A adjusts to increase the luminance of the regions designated by the line of sight of the user for the images and a part connecting the regions to each other. When the distance is equal to or larger than the threshold and the line of sight of the user moves between the regions, it will pass through a dark region, which requires pupil adjustment. To compare the regions with each other, performing a comparison without pupil adjustment is easier to find the difference. Thus, so as not to perform pupil adjustment, when the distance is equal to or larger than the threshold, the luminance of a range through which the line of sight of the user passes is adjusted to be increased.

When the regions of the images are positioned at the same height on the display screen, the luminance of a part which strides the images and extends in a lateral direction between the regions is adjusted to be increased. When the regions of the images are positioned at different heights on the display screen, the luminance of the part which strides the images and extends in a diagonal direction between the regions is adjusted to be increased.

The threshold is a constant value even if a size of the display screen of the display 12 or a size of an area of the displayed images changes. For example, the threshold may be set for each user who visually compares images with each other.

The following describes another example of the images 100 displayed on the display 12 by FIG. 8. In the state illustrated in FIG. 8, a region is designated by a line of sight E of the user. In the image $\mathbf{100}_1$ and the image $\mathbf{100}_2$, the entire luminance is reduced to adjust brightness. In the images 100, the luminance of the region $\mathbf{100}_1$P at the upper left of the image $\mathbf{100}_1$, the region $\mathbf{100}_2$ P at the upper left of the image $\mathbf{100}_2$, which are designated by the line of sight E of the user, and a part between the regions is adjusted to be increased.

The following describes processes in the diagnosis image reading apparatus 10A by FIG. 9. The processes at Step S121 to Step S126 and Step S130 to Step S134 are the same processes at Step S101 to Step S106 and Step S107 to Step S111 of the flowchart illustrated in FIG. 6.

The controller 20A measures the distance between the regions (Step S127). More specifically, by the distance measurement unit 26A, the controller 20A measures the distance between the regions designated by the line of sight of the user for the images. The controller 20A proceeds to Step S128.

The controller 20A determines whether the distance is equal to or larger than the threshold (Step S128). More specifically, if it is determined that the distance is equal to or larger than the threshold (Yes at Step S128), the controller 20A proceeds to Step S129. If it is not determined that the distance is equal to or larger than the threshold (No at Step S128), the controller 20A proceeds to Step S130.

If it is determined that the distance is equal to or larger than the threshold (Yes at Step S128), the controller 20A connects the regions to each other and adjusts the luminance (Step S129). More specifically, by the luminance adjustment unit 24A, the controller 20A adjusts to increase the luminance of the region designated by the line of sight of the user for the another image and a part connecting the designated region and the region of the original image before the movement of the line of sight in which the adjustment of luminance is maintained. The controller 20A proceeds to Step S131.

By Step S129, the display 12 displays, for example, the image $\mathbf{100}_1$ and the image $\mathbf{100}_2$ illustrated in FIG. 8. In the region $\mathbf{100}_1$P at the upper left of the image $\mathbf{100}_1$, the region $\mathbf{100}_2$P at the upper left of the image $\mathbf{100}_2$, and the part connecting the regions to each other, the luminance is adjusted to be increased.

As described above, in the present embodiment, when the distance between the regions designated by the line of sight of the user is equal to or larger than the threshold, the luminance of the part connecting the regions to each other can be adjusted to be increased. According to the present embodiment, there is no difference in brightness when the line of sight of the user moves between the regions in order to visually compare two images with each other, thus making it easy to perform the comparison without performing pupil adjustment.

Third Embodiment

Figure 10:
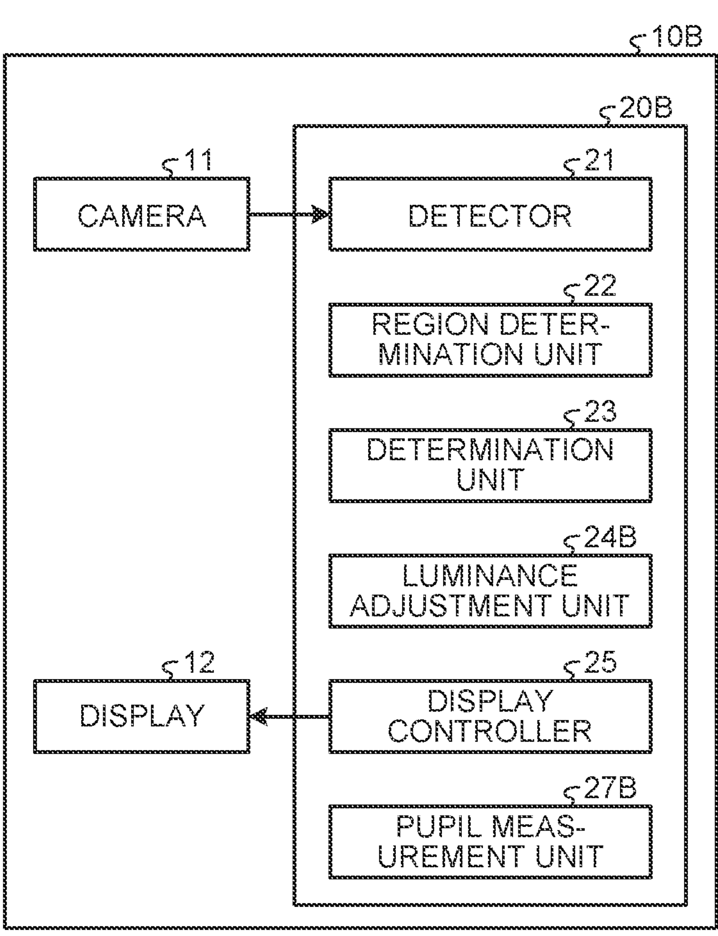
FIG. 10 is a block diagram of a configuration example of a diagnosis image reading apparatus having a diagnosis image reading control apparatus according to a third embodiment.

The following describes a diagnosis image reading apparatus 10B having a controller 20B according to the present embodiment with reference to FIG. 10 and FIG. 11. FIG. 10 is a block diagram of a configuration example of the diagnosis image reading apparatus 10B having the controller 20B according to a third embodiment. FIG. 11 is a flowchart of an example of processes in the controller 20B according to the third embodiment. The diagnosis image reading apparatus 10B is similar to the diagnosis image reading apparatus 10 according to the first embodiment in its basic configuration. In the following description, components similar to those of the diagnosis image reading apparatus 10 are denoted by the same symbols or corresponding symbols, and detailed descriptions thereof are omitted. The controller 20B according to the present embodiment differs from that of the first embodiment in that the controller 20B has a pupil measurement unit 27B and different processes in a luminance adjustment unit 24B.

The pupil measurement unit 27B measures a size of the pupil of the user. More specifically, the pupil measurement unit 27B measures the size of the pupil of the user based on the user image captured by the camera 11. For the method for measuring the size of the pupil of the user based on the user image, known methods can be used, without limitation.

When the respective regions designated by the line of sight of the user for the images are visually recognized alternately and the size of the pupil exceeds a threshold, the luminance adjustment unit 24B adjusts to increase the luminance of a part connecting the regions designated by the line of sight of the user for the images to each other. More specifically, when the detector 21 detects that the line of sight is moving between the respective regions designated by the line of sight of the user for the images and the size of the pupil exceeds the threshold based on the measurement result of the pupil measurement unit 27B, the luminance adjustment unit 24B adjusts to increase the luminance of the part connecting the regions to each other.

When the size of the pupil of the user exceeds the threshold, pupil adjustment is being performed. Thus, so as to enable a comparison between the images without performing pupil adjustment, when the size of the pupil exceeds the threshold, the luminance of a range through which the line of sight of the user passes is adjusted to be increased.

The threshold for the size of the pupil may be, for example, a preset certain value. The threshold for the size of the pupil may be, for example, a value larger than a certain percentage of the size of the pupil when an image with normal brightness is viewed.

The following describes processes in the diagnosis image reading apparatus 10B by FIG. 11. The processes at Step S141 to Step S147 and Step S151 to Step S154 are the same processes at Step S101 to Step S107 and Step S108 to Step S111 of the flowchart illustrated in FIG. 6.

The controller 20B measures the size of the pupil (Step S148). More specifically, by the pupil measurement unit 27B, the controller 20B measures the size of the pupil of the user. The controller 20B proceeds to Step S149.

The controller 20B determines whether the size of the pupil exceeds the threshold (Step S149). More specifically, if it is determined that the size of the pupil exceeds the threshold (Yes at Step S149), the controller 20B proceeds to Step S150. If it is not determined that the size of the pupil exceeds the threshold (No at Step S149), the controller 20B proceeds to Step S151.

If it is determined that the size of the pupil exceeds the threshold (Yes at Step S149), the controller 20B connects the regions to each other and adjusts the luminance (Step S150). More specifically, by the luminance adjustment unit 24B, the controller 20B adjust to increase the luminance of the part connecting the regions designated by the line of sight of the user for the images to each other. The controller 20B proceeds to Step S151.

By Step S149, the display 12 displays, for example, the image $\mathbf{100}_1$ and the image $\mathbf{100}_2$ illustrated in FIG. 8.

As described above, in the present embodiment, when the regions designated by the line of sight of the user for the images are visually recognized alternately and the size of the pupil exceeds the threshold, the luminance of the part connecting the regions to each other can be adjusted to be increased. According to the present embodiment, there is no difference in brightness when the line of sight of the user moves between the regions, and thus a change in the size of the pupil can be reduced.

The components of the illustrated diagnosis image reading apparatuses are functionally conceptual and are not necessarily required to be physically configured as illustrated. That is, the specific form of each apparatus is not limited to that illustrated but may be functionally or physically distributed or integrated in arbitrary units in whole or in part in accordance with the processing load, the use condition, and the like of each apparatus.

The configuration of the diagnosis image reading apparatus is, for example, implemented as software by a computer program loaded into memory. The above embodiments are described as functional blocks implemented by the coordination of this hardware or software. That is, these functional blocks can be implemented in various forms by hardware alone, software alone, or a combination of the two.

The components described above include those that can be readily assumed by those skilled in the art and those that are substantially identical thereto. Further, the configurations described above can be combined with each other as appropriate. Various omissions, replacements, or modifications of the configurations are possible without departing from the gist of the present application.

In the processing of the flowchart illustrated in FIG. 9 above, after being determined to be Yes at Step S126, Step S130 may be executed before proceeding to Step S127. In this case, the distance between the regions may be measured at Step S127 after adjusting the luminance of the region of the other image at Step S130.

The present application can be used for a diagnosis image reading apparatus, which is an apparatus for reading images to be read in radiography or mammography, for example.

The present disclosure includes matters contributing to the realization of "health and well-being for all" of the Sustainable Development Goals (SDGs) and contributing to value creation through healthcare products and services.

The present application can adjust luminance of a screen appropriately in accordance with a region of an image.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A diagnosis image reading control apparatus comprising:

at least one memory that is configured to store computer executable instructions; and at least one processor that is configured to execute the computer executable instructions to perform operations, comprising:

displaying multiple images on a display as a function of a display controller;

determining that the multiple images are displayed on the display, based on an image signal output from the display controller, as a function of a determination unit;

detecting a line of sight of a user on the display as a function of a detector;

dividing each of the multiple images into multiple regions and identifying regions in which the line of sight of the user is positioned as a function of a region determination unit; and adjusting to increase luminance of the regions identified by the line of sight of the user in the multiple images as a function of a luminance adjustment unit.

2. The diagnosis image reading control apparatus according to claim 1, wherein the operations further comprise measuring a distance between the regions identified by the line of sight of the user in the images as a function of a distance measurement unit, and the adjusting further comprises adjusting, in a case wherein the distance is equal to or larger than a threshold, to increase luminance of a part which strides the images and extends in a lateral direction between the regions and a part which strides the images and extends in a diagonal direction between the regions.

3. The diagnosis image reading control apparatus according to claim 1, wherein the operations further comprise measuring a size of a pupil of the user as a function of a pupil measurement unit, wherein the detecting further comprises detecting that the line of sight of the user is moving between the identified regions in the multiple images as the function of the detector, and when it is determined that the size of the pupil exceeds a threshold, the adjusting further comprises adjusting to increase luminance of a part connecting the identified regions as the function of the luminance adjustment unit.

4. A diagnosis image reading control method comprising:

displaying multiple images on a display simultaneously;

determining that the multiple images are displayed on the display based on an image signal output;

detecting a line of sight of a user on the display;

dividing each of the multiple images into multiple regions and identifying regions in which the line of sight of the user is positioned; and adjusting luminance of the images, wherein the adjusting further comprises adjusting to increase luminance of the regions identified by the line of sight of the user in the multiple images.

5. A non-transitory computer-readable storage medium that stores a computer program executable by a computer operating as a diagnosis image reading apparatus in which the diagnosis image reading control method according to claim 4 is performed.

* * * * *